(12) United States Patent
Shibuya et al.

(10) Patent No.: US 11,860,177 B2
(45) Date of Patent: Jan. 2, 2024

(54) ANALYSIS METHOD OF AUTOMATIC ANALYZER

(71) Applicant: HITACHI HIGH-TECH CORPORATION, Tokyo (JP)

(72) Inventors: Satoshi Shibuya, Tokyo (JP);
Tsuguhiko Satou, Tokyo (JP);
Toshihide Hanawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 371 days.

(21) Appl. No.: 16/921,997

(22) Filed: Jul. 7, 2020

(65) Prior Publication Data
US 2020/0333367 A1 Oct. 22, 2020

Related U.S. Application Data

(63) Continuation of application No. 15/552,809, filed as application No. PCT/JP2016/052846 on Feb. 1, 2016, now Pat. No. 10,746,755.

(30) Foreign Application Priority Data

Feb. 24, 2015 (JP) .................................. 2015-033482

(51) Int. Cl.
*G01N 35/02* (2006.01)
*G01N 35/04* (2006.01)
(Continued)

(52) U.S. Cl.
CPC .......... *G01N 35/026* (2013.01); *G01N 33/48* (2013.01); *G01N 35/00* (2013.01); *G01N 35/02* (2013.01);
(Continued)

(58) Field of Classification Search
CPC ......... G01N 35/0092; G01N 35/00603; G01N 35/026; G01N 35/04; G01N 35/02;
(Continued)

(56) References Cited

U.S. PATENT DOCUMENTS 5,972,295 A 10/1999 Hanawa et al.
6,019,945 A 2/2000 Ohishi et al.
(Continued)

FOREIGN PATENT DOCUMENTS

EP 0445616 A2 2/1991
JP 3255366 11/1991
(Continued)

OTHER PUBLICATIONS

Japanese Office Action received in corresponding Japanese Application No. 2019-189140 dated Oct. 6, 2020.
(Continued)

*Primary Examiner* — Kyle O Logan
(74) *Attorney, Agent, or Firm* — Mattingly & Malur, PC

(57) ABSTRACT

An analysis method of an automatic analyzer is provided. The automatic analyzer includes: an insertion unit into which a rack is inserted; a transport line that transports the rack; a detection unit that detects a rack identifier from a rack or an attribute from a sample container which accommodates therein a sample as an object to be examined and which is mounted on a rack; an analysis module that includes a light source and a spectrometer which measures a measurement value to analyze a sample; a rack standby unit in which a rack stands by; and, a rack recovery unit that recovers a rack. In the automatic analyzer, a rack stands by in the rack standby unit until a measurement result in the analysis module is output; and is then recovered to the rack recovery unit. The analysis method includes: a step of transporting a rack from the rack insertion unit to the
(Continued)

transport line, making the transported rack stand by until a measurement result in the analysis module is output, and then recovering the rack to the rack recovery; a step of detecting an identifier from the rack or an attribute from a sample container accommodating a sample and mounted on the rack; and a step of, when a rack transported subsequent to the rack of interest is transported from the rack insertion unit to the transport line, recovering the subsequent rack to the rack recovery unit without standing by in the rack standby unit.

12 Claims, 11 Drawing Sheets

(51) Int. Cl.
*G01N 35/00* (2006.01)
*G01N 33/48* (2006.01)

(52) U.S. Cl.
CPC ... *G01N 35/04* (2013.01); *G01N 2035/00752* (2013.01); *G01N 2035/0493* (2013.01)

(58) Field of Classification Search
CPC ...... G01N 35/10; G01N 35/00; G01N 35/021; G01N 2035/00725; G01N 2035/0493; G01N 2035/0462; G01N 2035/00851; G01N 2035/0467; G01N 2035/0472; G01N 2035/0094; G01N 2035/0406; G01N 2035/041; G01N 2035/0415; G01N 2035/0465; G01N 2035/00504; G01N 1/312; G01N 1/2813; G01N 15/05; G01N 21/51; G01N 2021/5973; G01N 2035/0413; G01N 2035/0096
See application file for complete search history.

(56) References Cited

U.S. PATENT DOCUMENTS

| | | | | |
|---|---|---|---|---|
| 2009/0142844 | A1* | 6/2009 | Le Comte | G01N 35/04 901/6 |
| 2010/0212438 | A1 | 8/2010 | Tanaka | |
| 2011/0290040 | A1* | 12/2011 | Tatsutani | G01N 35/026 73/863.01 |
| 2012/0294765 | A1* | 11/2012 | Watabe | G01N 35/026 422/65 |
| 2013/0316461 | A1 | 11/2013 | Fujita | |
| 2014/0234949 | A1* | 8/2014 | Wasson | B01L 3/50851 422/519 |
| 2015/0185119 | A1* | 7/2015 | Nagai | B01L 3/5082 422/63 |

FOREIGN PATENT DOCUMENTS

| | | |
|---|---|---|
| JP | 10213586 | 8/1998 |
| JP | 10325839 | 12/1998 |
| JP | 2008046095 A | 2/2008 |
| JP | 2009270869 A | 11/2009 |
| JP | 2010181197 A | 8/2010 |

OTHER PUBLICATIONS

International Search Report of PCT/JP2016/052846 dated May 17, 2016.

* cited by examiner

[Fig. 1]
[Fig. 2]
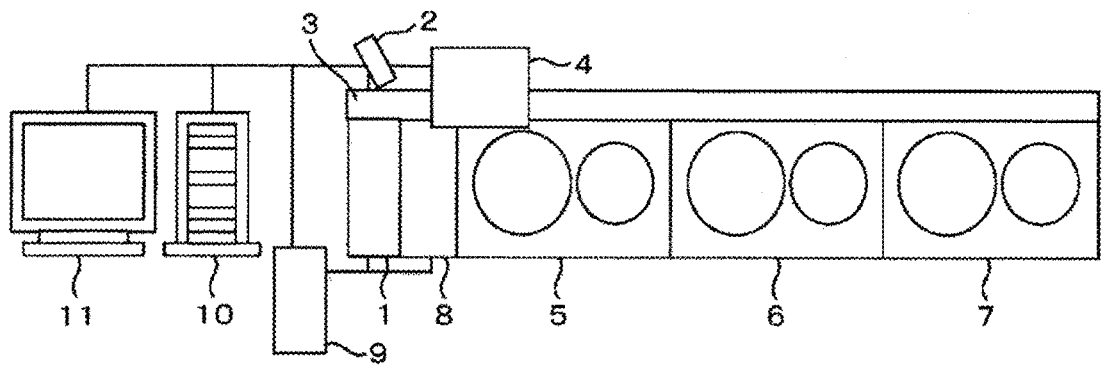

[Fig. 3]
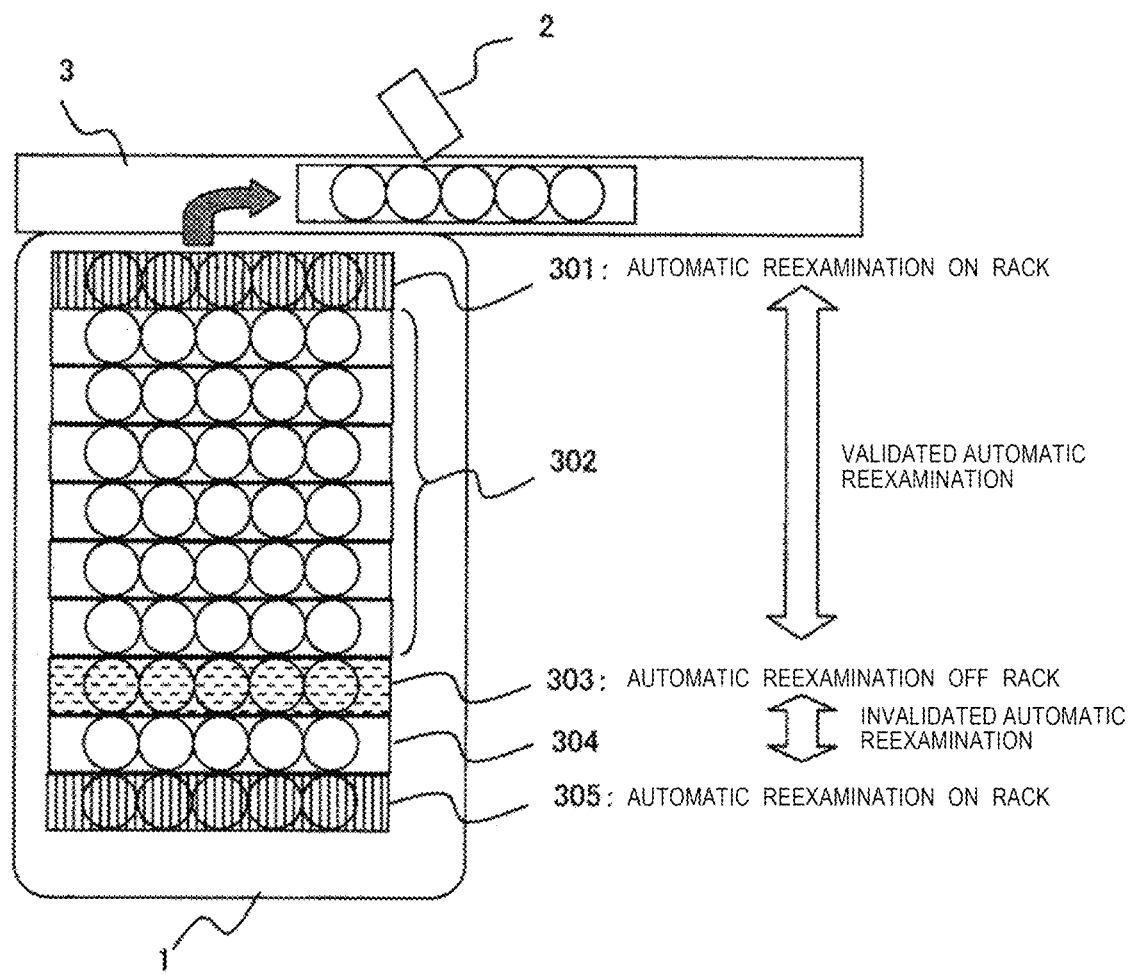

[Fig. 4]
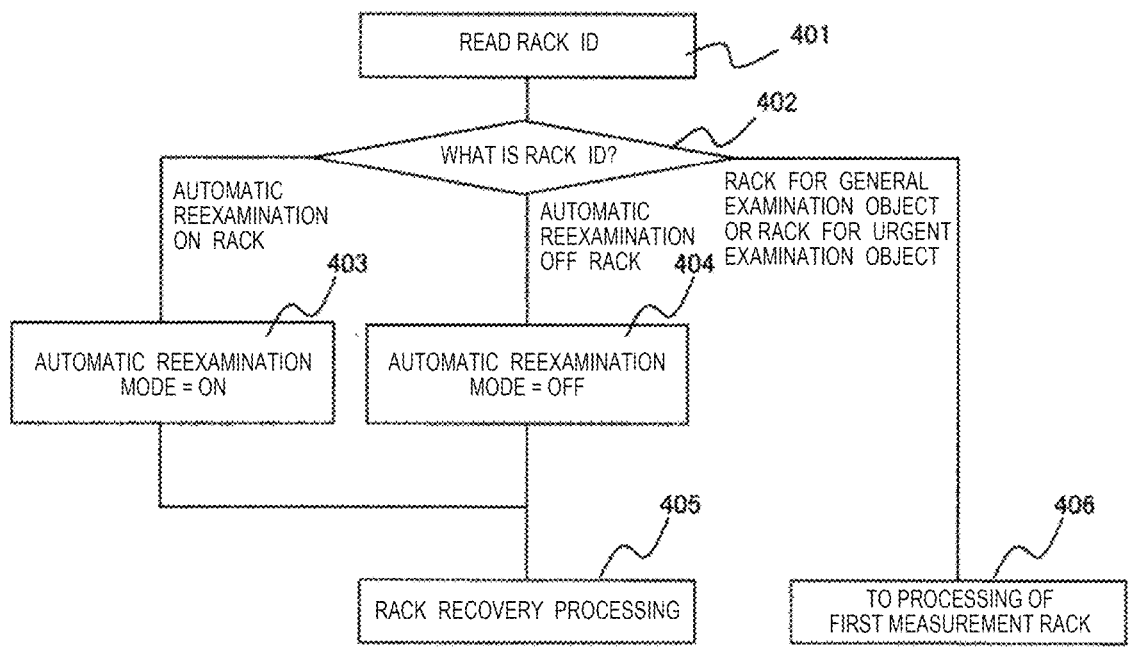

[Fig. 5]
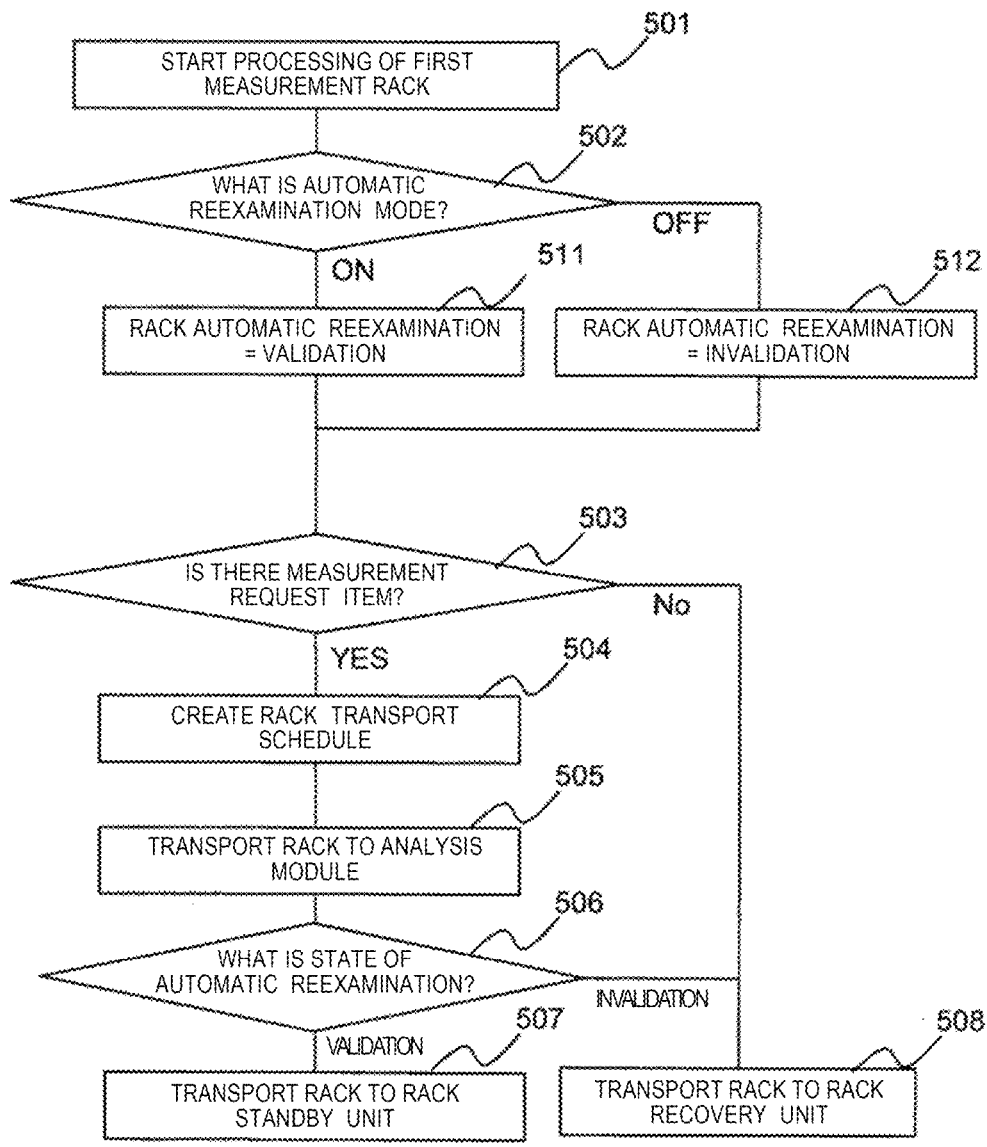

[Fig. 6]
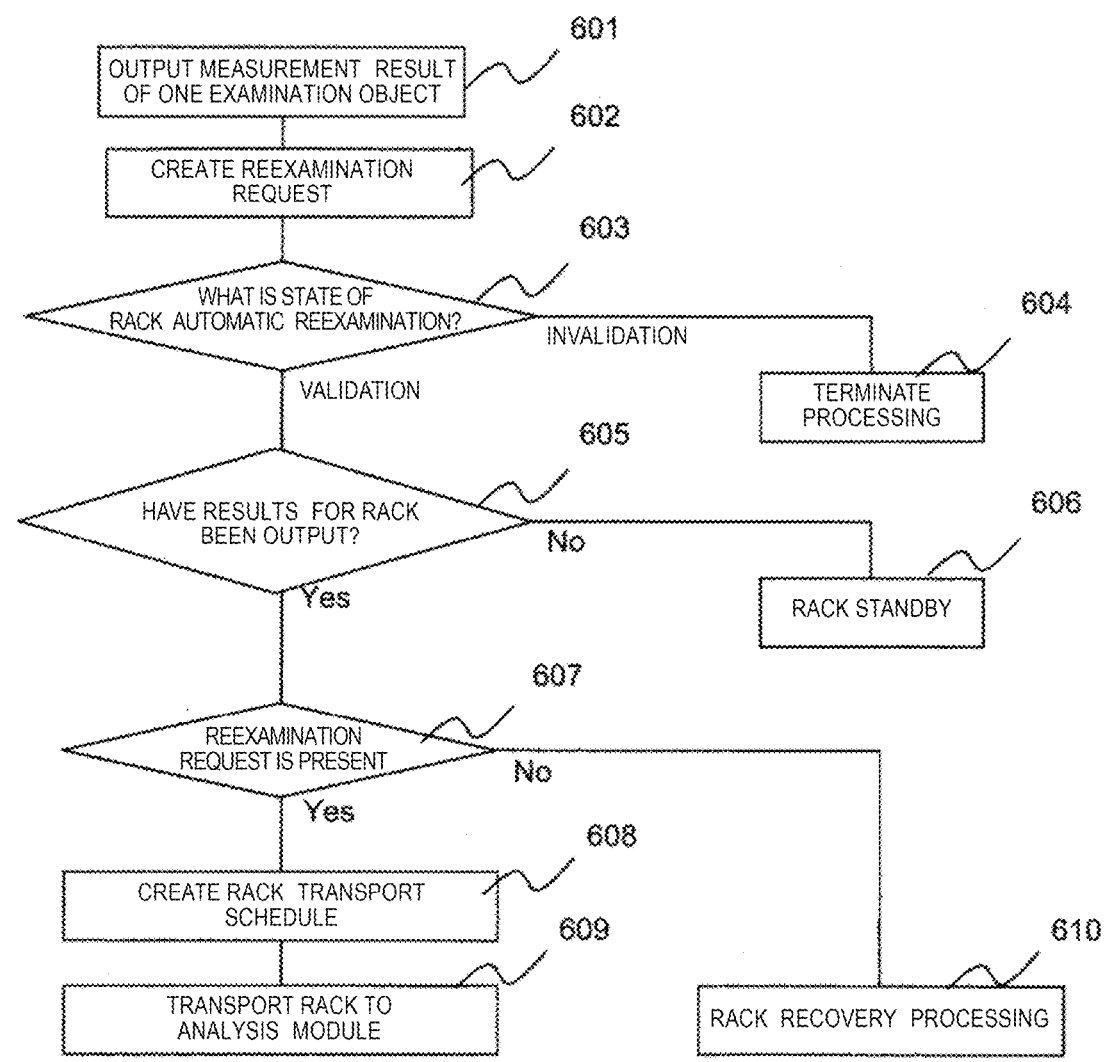

[Fig. 7]
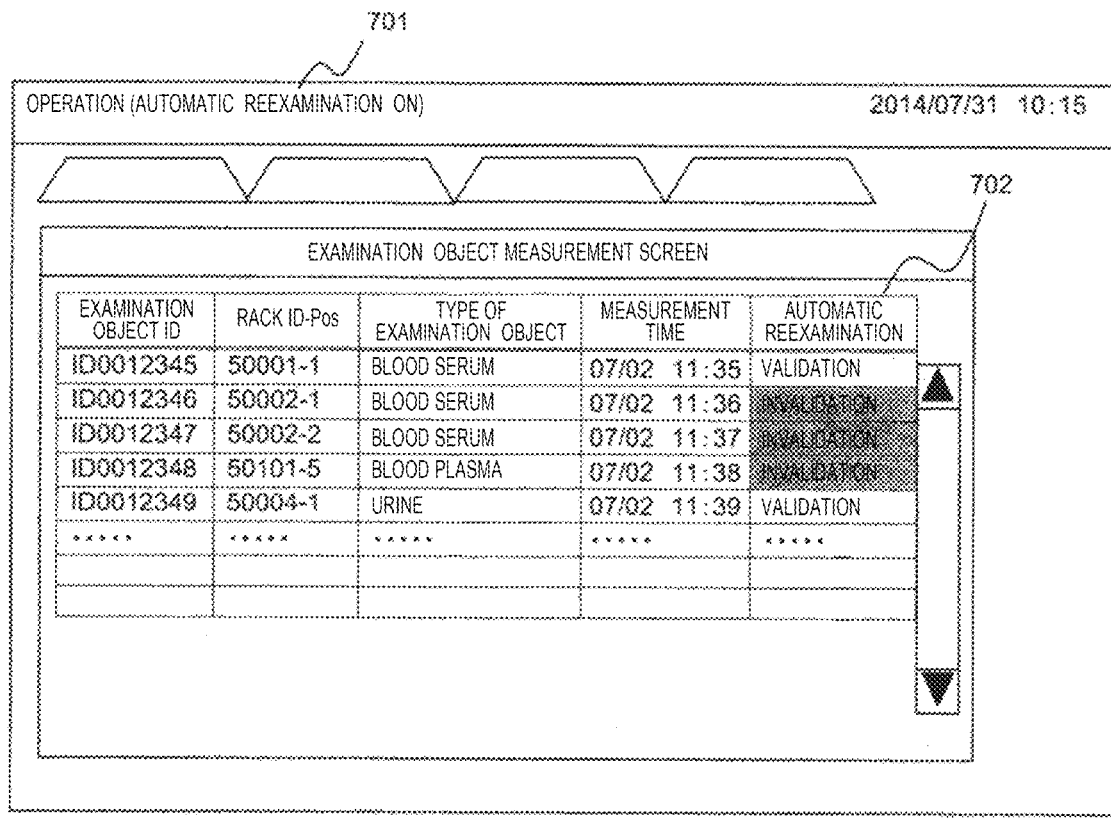
[Fig. 8]
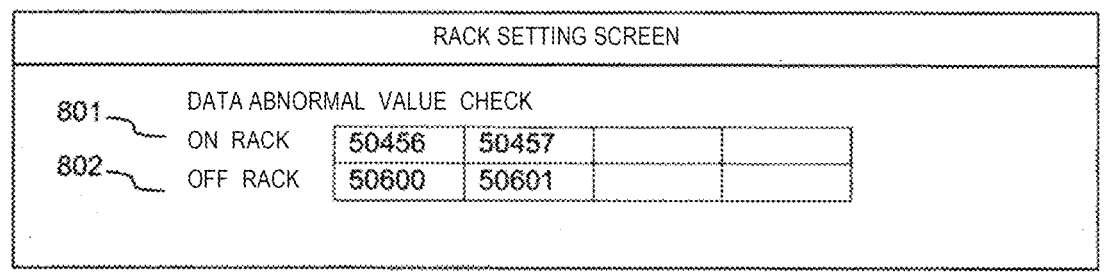

[Fig. 9]
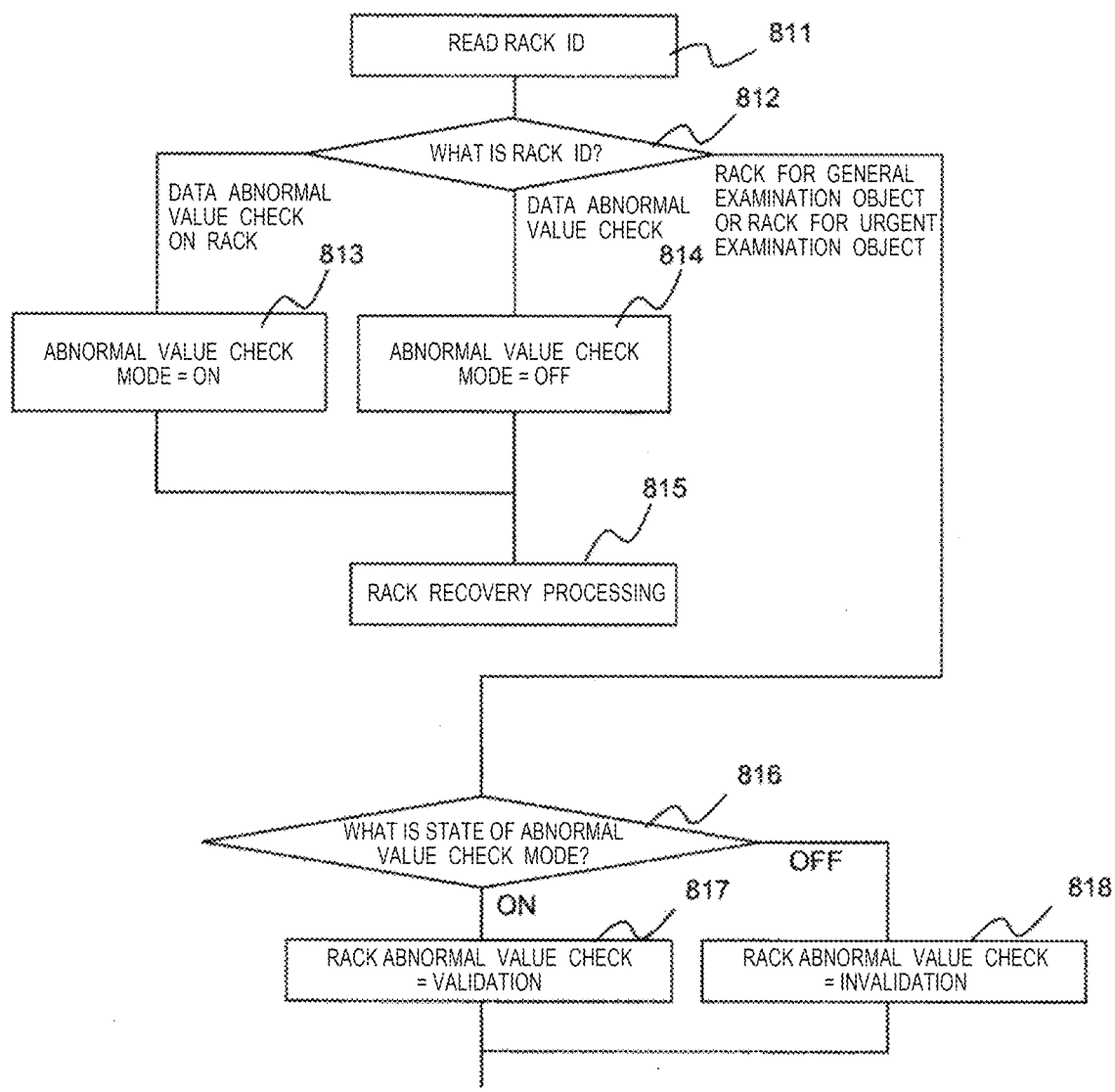

[Fig. 10]
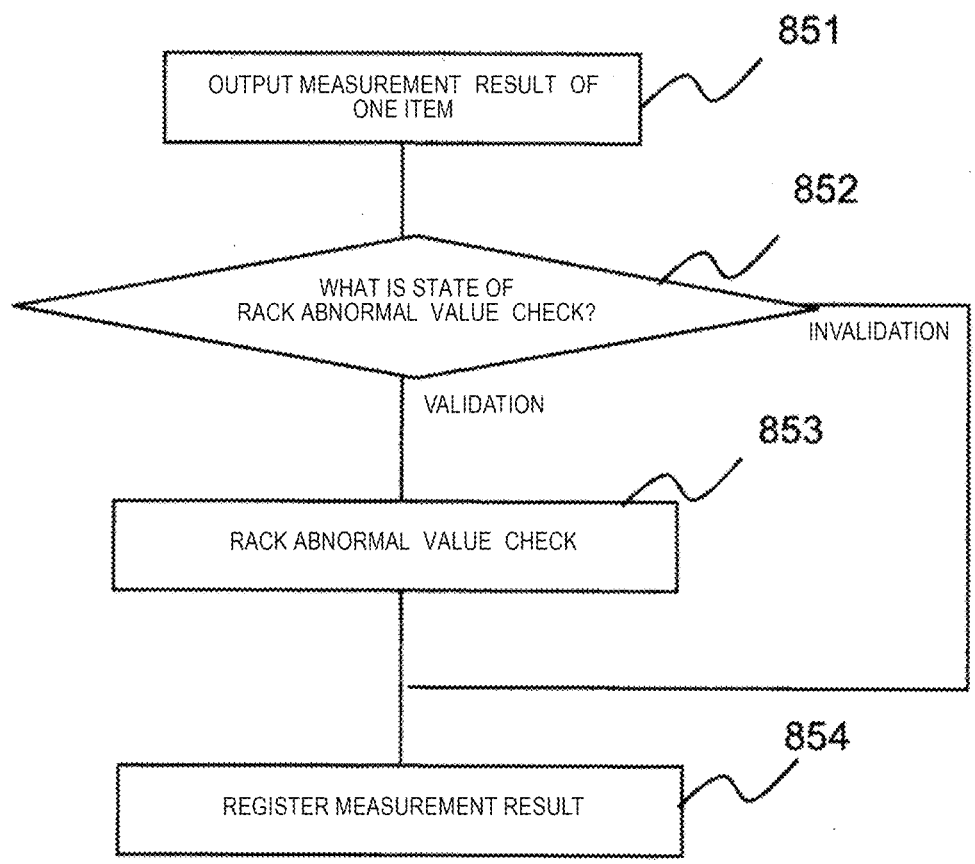
[Fig. 11]
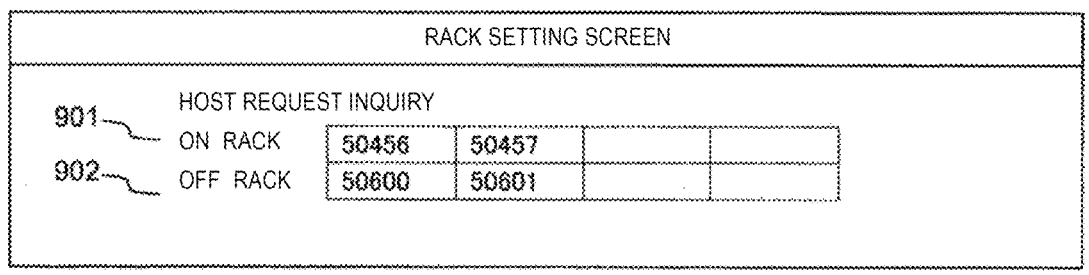

[Fig. 12]
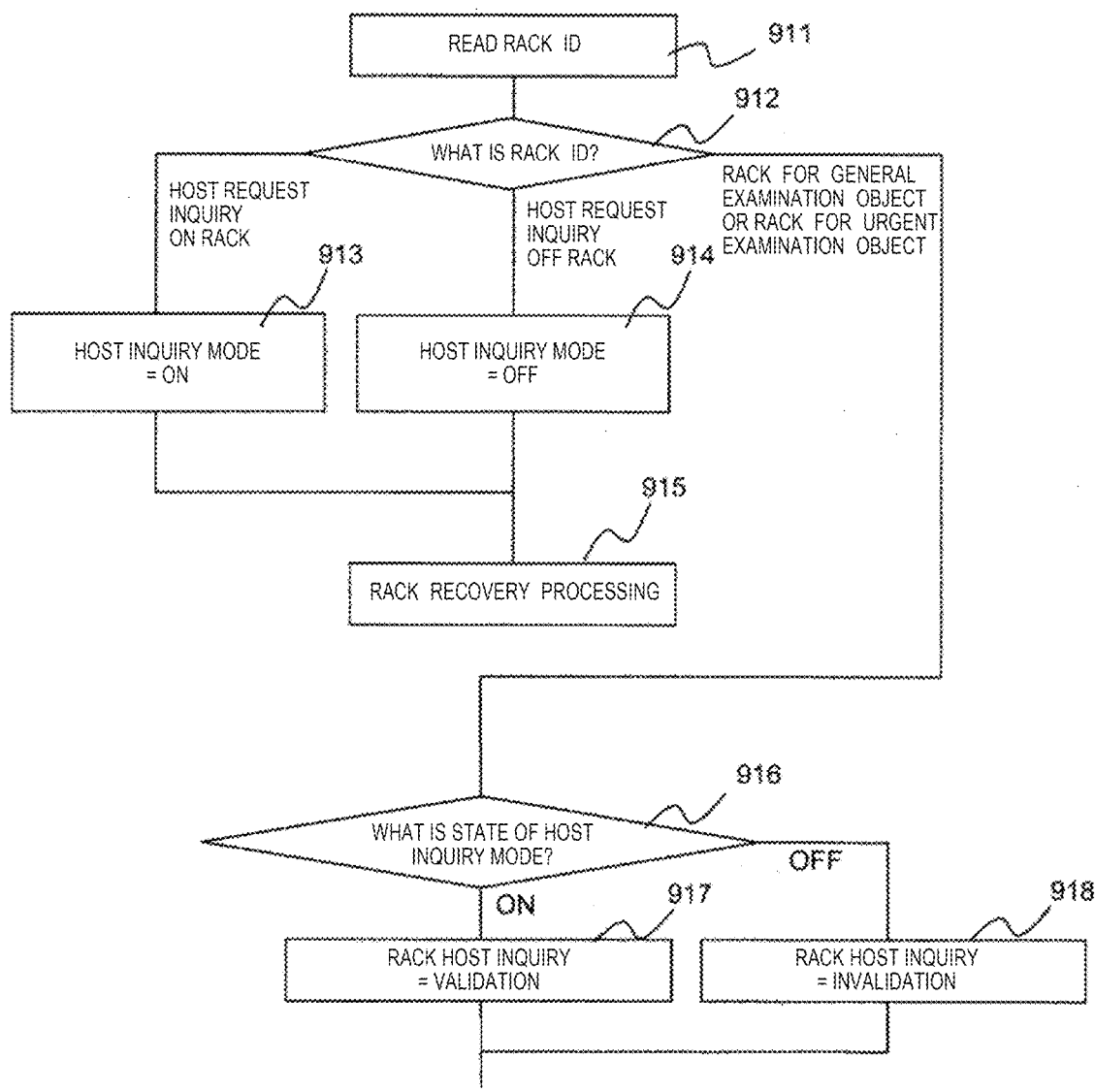

[Fig. 13]
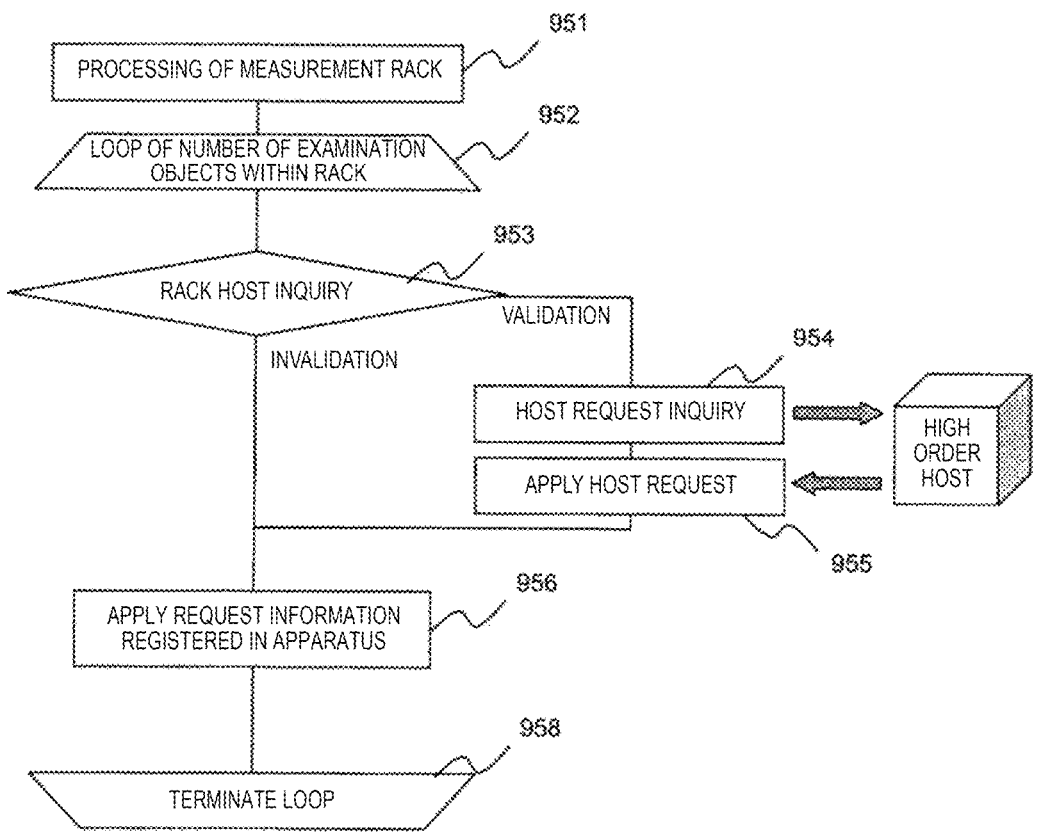

[Fig. 14]
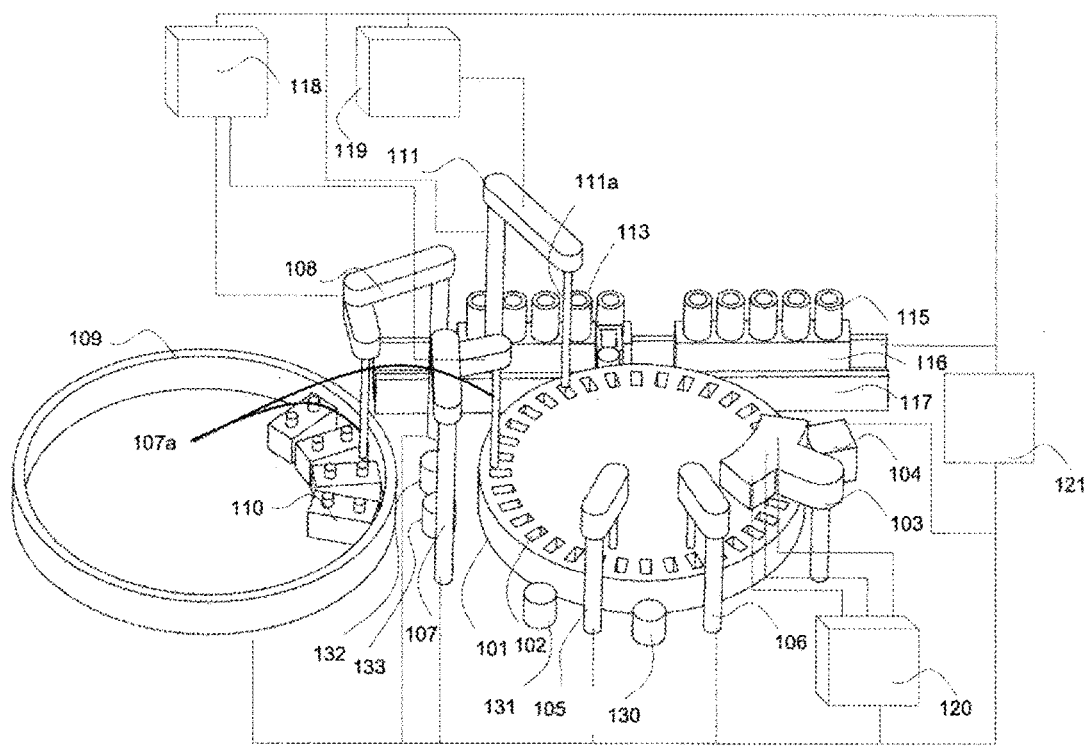

ANALYSIS METHOD OF AUTOMATIC ANALYZER

TECHNICAL FIELD

The present invention relates to an automatic analyzer that performs quantitative analysis and qualitative analysis of a biological sample such as blood and urine, and more particularly, to an automatic analysis system including a transport apparatus that transports a sample container to an analyzer.

BACKGROUND ART

An automatic analyzer that automatically performs quantitative analysis and qualitative analysis of a biological sample such as blood and urine has become drastically widespread centering on large hospitals and clinical examination stations which need to process a large number of examination objects of patients to be examined in a short time, and various types of large, medium, and small-sized automatic analyzers have been developed depending on processing capabilities thereof. In particular, a large-sized apparatus that analyzes and processes a large number of examination objects may transport a plurality of examination object containers each having an examination object put thereinto to a plurality of analyzers through a transport line (transport apparatus) in a state where the examination object containers are held in a holder called an examination object rack. In such an apparatus, a laboratory technician automatically executes the output of an analysis result by only inserting the examination object rack into an examination object rack insertion port.

In this case, a type of rack and an examination object are recognized and analyzed by a bar code reading apparatus on the transport line during the transport of the examination object rack inserted into the examination object rack insertion port through the transport line having a belt conveyor shape. As such an automatic analysis system, an automatic analysis system as disclosed in, for example, PTL 1 is known.

In addition, as disclosed in PTL 2, a plurality of analysis units are disposed along a transport line constituted by a belt conveyor, a rack supply unit is disposed on one end side of the transport line, and a rack recovery unit is disposed on the other end side thereof. In addition, a rack standby unit is disposed at the front of the rack recovery unit so that reexamination can be automatically performed.

In addition, an automatic analyzer as disclosed in PTL 3 is known. The automatic analyzer classifies types of examination objects for each examination object rack to consistently perform automation from the transport of a plurality of types of samples (examination objects) accommodated in sample containers for the respective types to the registration of measurement data of analysis results during the operation of the same analysis system.

CITATION LIST

Patent Literature

PTL 1: JP-A-10-325839
PTL 2: JP-A-10-213586
PTL 3: JP-A-03-255366

SUMMARY OF INVENTION

Technical Problem

In such an automatic analyzer, in a case where a measurement result is abnormal, the apparatus itself has an automatic reexamination function of automatically performing remeasurement. Each facility is operated by switching between validation and invalidation of the automatic reexamination depending on operation.

A situation often occurs in which the measurement of an examination object, such as an extremely small amount of examination object, which is not desired to be subjected to automatic reexamination is performed during operation in validated automatic reexamination. The automatic reexamination function is a function of causing the apparatus to determine the necessity of remeasurement on the basis of a first measurement result and to automatically perform remeasurement. An examination object stands by in a rack standby unit until at least the first measurement result is output, and cannot be taken out from the apparatus. The extremely small amount of examination object is not often sufficient to be subjected to remeasurement, and is desired to be immediately taken out from the apparatus as soon as possible after the dispensing of the examination object in the first measurement is terminated. In addition, the examination object desired to be immediately taken out from the apparatus wastefully stays in the apparatus, which causes the retardation of the rack and a decrease in a throughput of the measurement. In addition, a time is required for the measurement, such as in a case where the same examination object container is desired to be used for measurement in another analyzer as it is.

For this reason, in a case of such an examination object, there is a demand that measurement is desired to be performed by invalidating automatic reexamination. However, in the present situation, in a case where an automatic reexamination mode is switched, it is necessary to return the apparatus from a measurement state to a standby state, and thus a time is required for remeasurement.

As a solution therefor, means for adding validation and invalidation information of automatic reexamination to examination object information to be measured is considered. However, in a case of a rack on which a plurality of examination object containers can be mounted, when an automatic reexamination-validated examination object and an automatic reexamination-invalidated examination object are installed together in one rack, even the automatic reexamination-invalidated examination object cannot be taken out until a first measurement result for the automatic reexamination-validated examination object is output, which results in an inconvenient situation. For this reason, useability is more improved when automatic reexamination is switched in units of racks than when automatic reexamination is switched in units of examination objects.

In a case where switching is performed in units of racks, there is consideration of means for defining the range of an automatic reexamination-invalidated rack ID in advance, similarly to a case where a range of a rack ID for identifying an examination object rack is defined for each type of examination object in the present situation, and invalidating automatic reexamination of an examination object mounted on the examination object rack by recognizing the rack ID.

However, in this case, since the range of the rack ID is defined for each of a plurality of types of examination objects, and the range of an automatic reexamination-invalidated rack ID is defined for each type of examination object, it is necessary to perform range setting by an extent of a number obtained by multiplying the types of examination objects and the validation or invalidation of automatic reexamination together, and the range of the rack ID becomes complicated, which may result in a concern that an operator mounts an examination object on a wrong examination object rack.

In addition, since the number of times of measurement of an extremely small amount of examination object changes depending on a situation of the day, the setting of a narrow range of the rack ID may result in the insufficiency of examination object racks, and the setting of a wide range of the rack ID may result in the other unusable examination object racks.

An object of the invention is to provide an analysis method of an automatic analyzer capable of switching between validation and invalidation of automatic reexamination without stopping measurement by efficiently using an examination object rack. Further, another object of the invention is to provide an analysis method of an automatic reanalyzer capable of switching between various apparatus operation modes by using an examination object rack other than switching between validation and invalidation of automatic reexamination.

Solution to Problem

A representative configuration of the invention for accomplishing the above-described objects is as follows.

An analysis method of an automatic analyzer is provided. The automatic analyzer includes: an insertion unit into which a rack is inserted; a transport line that transports the rack; a detection unit that detects a rack identifier from a rack or an attribute from a sample container which accommodates therein a sample as an object to be examined and which is mounted on a rack; an analysis module that includes a light source and a spectrometer which measures a measurement value to analyze a sample; a rack standby unit in which a rack stands by; and, a rack recovery unit that recovers a rack. In the automatic analyzer, a rack stands by in the rack standby unit until a measurement result in the analysis module is output; and is then recovered to the rack recovery unit. The analysis method includes: a step of transporting a rack from the rack insertion unit to the transport line, making the transported rack stand by until a measurement result in the analysis module is output, and then recovering the rack to the rack recovery; a step of detecting an identifier from the rack or an attribute from a sample container accommodating a sample and mounted on the rack; and a step of, when a rack transported subsequent to the rack of interest is transported from the rack insertion unit to the transport line, recovering the subsequent rack to the rack recovery unit without standing by in the rack standby unit.

The operation mode switching rack may be defined as two types of an operation mode ON rack and an operation mode OFF rack, and one type of operation mode may be defined as the operation mode switching rack so that switching between turn-on and turn-off of the operation mode is performed for every recognition of the rack.

In addition, the operation mode switching rack may perform switching in both cases of a general examination object and an urgent examination object, or switching may be performed separately in an operation mode switching rack of a general examination object and an operation mode switching rack of an urgent examination object.

In addition, the operation mode switching rack is not limited to a rack that transports an examination object, and may be a rack, having a rack ID attached thereto, which is capable of being transported through a transport line.

In addition, the identification of the operation mode switching rack may be performed using a rack exclusively used for switching instead of using the rack ID. In this case, a rack shape exclusively used for switching which is different from a normal rack shape used for measurement is used, and means for identifying the rack shape may be provided so as to recognize the rack exclusively used for switching and switch an operation mode.

In addition, as the rack exclusively used for switching, coating with special color is performed, and a sensor that recognizes the coating color of the rack may be provided so as to recognize the rack exclusively used for switching and switch an operation mode.

In addition, the identification of the operation mode switching rack may be performed so as to switch an operation mode by installing a test tube, having a bar code for switching an operation mode attached thereto, on the rack and recognizing the bar code of the test tube, instead of using the rack ID.

Advantageous Effects of Invention

According to the invention, a rack is used as a switch for switching an apparatus operation mode such as an automatic reexamination mode, and thus it is possible to efficiently use the rack to be used for operation and to switch an operation mode while continuing measurement.

In addition, it is possible to alleviate the retardation of the rack in an apparatus by automatic reexamination standby, to take out an examination object from the apparatus without waiting for the output of a measurement result, and to efficiently perform operation.

In addition, it is not necessary to perform range setting of a rack ID by multiplying the type of examination object and the validation or invalidation of automatic reexamination together, which eliminates a concern that an operator mounts an examination object on a wrong examination object rack due to the complication of the range of the rack ID.

In addition, an operation mode switching rack is inserted when racks are installed side by side in a supply tray in order of insertion so that it is easy to visually know from which rack an operation mode is to be switched before the insertion into the apparatus, and thus it is possible to easily prevent an erroneous operation.

BRIEF DESCRIPTION OF DRAWINGS

FIG. 1 is a schematic diagram illustrating the entire configuration of an automatic analyzer according to an embodiment of the invention.

FIG. 2 illustrates a screen for setting a rack ID of an automatic reexamination switching rack according to a first embodiment.

FIG. 3 illustrates an example of the installation of a rack in a rack insertion unit according to the first embodiment.

FIG. 4 illustrates a flow of identification processing of the automatic reexamination switching rack according to the first embodiment.

FIG. 5 illustrates a flow of automatic reexamination switching processing during first measurement according to the first embodiment.

FIG. 6 illustrates a flow of automatic reexamination switching processing during reexamination measurement according to the first embodiment.

FIG. 7 illustrates a screen on which the state of automatic reexamination according to the first embodiment is displayed.

FIG. 8 illustrates a screen for setting a rack ID of a switching rack of a data abnormal value check according to a second embodiment.

FIG. 9 illustrates a flow of identification processing of the switching rack of the data abnormal value check according to the second embodiment.

FIG. 10 illustrates a flow of data abnormal value check processing during the output of a measurement result according to the second embodiment.

FIG. 11 illustrates a screen for setting a switching rack ID of host request inquiry according to a third embodiment.

FIG. 12 illustrates a flow of switching processing of host request inquiry according to the third embodiment.

FIG. 13 illustrates a flow of host request inquiry processing according to the third embodiment.

FIG. 14 is a perspective view illustrating the entire configuration of an analysis module according to an embodiment of the invention.

DESCRIPTION OF EMBODIMENTS

Hereinafter, embodiments for implementing the invention will be described.

An operation mode used in an example refers to various modes such as a method of performing control on an object to be transported such as an examination object rack carried into an apparatus, a method of performing display when a certain condition is satisfied, and whether or not the apparatus and a host communicate with each other. The operation modes include a mode in which the apparatus executes or does not execute predetermined control (the control includes the control of transport of the examination object rack, the control of notification, the control of display, and the like) automatically when a certain condition is satisfied, and a mode in which the apparatus automatically executes control different from that when the certain condition is satisfied.

In addition, regarding an operation mode switching rack, since it is not assumed that a general examination object is loaded thereon, unlike a rack for a general examination object. Accordingly, the operation mode switching rack may have a shape and structure that do not allow a general examination object to be loaded thereon, but will be called a rack in this specification for convenience of description.

In addition, the operation mode switching rack is a member for notifying the apparatus of the switching of an operation mode, and may have a structure capable of being carried into the apparatus. Since the operation mode switching rack has a structure capable of being carried into the apparatus, the operation mode switching rack is a member having at least the same longitudinal and lateral lengths of the bottom surface as those of a general examination object rack.

Example 1

In a first embodiment, an example in which an operation mode is switched in an operation mode switching rack will be described. Here, an example of the operation mode is an automatic reexamination mode. The first embodiment will be described with reference to FIGS. 1 to 8 showing the example.

FIG. 1 is a schematic diagram illustrating the entire configuration of an automatic analyzer according to an embodiment of the invention.

An automatic analysis system (automatic analyzer) according to this embodiment includes an examination object rack insertion unit 1, an ID reading unit 2, a transport line 3, an examination object rack standby unit 4, analysis modules 5, 6, and 7, an examination object rack recovery unit 8, and an overall management computer 9.

The examination object rack insertion unit 1 is a portion that inserts a plurality of examination object racks that respectively hold a plurality of examination objects (samples). The analysis modules 5, 6, and 7 are disposed along the transport line 3 and are removably connected to the transport line 3. The number of analysis modules can be arbitrarily set, and a case of three analysis modules is described in this embodiment.

The transport line 3 transports the examination object rack to the analysis modules 5, 6, and 7 in response to an analysis request from the examination object rack insertion unit 1 or transports the examination object rack to the examination object rack standby unit 4 that holds an examination object having been analyzed in the analysis modules 5, 6, and 7, or transports an examination object rack, for which an analysis request has not been given, to the examination object rack recovery unit 8.

In addition, the automatic analysis system includes an overall management computer 9 that performs necessary control within the examination object rack insertion unit 1, the ID reading unit 2, the transport line 3, the examination object rack standby unit 4, and the examination object rack recovery unit 8. An operation unit 10 for inputting necessary information and a display unit 11 that displays an analysis result are further connected to the overall management computer 9. In addition, the overall management computer 9 is provided with a storage unit that stores an operation mode of the automatic analyzer, and a control unit that controls the apparatus on the basis of the operation mode stored in the storage unit. In addition, the control unit can switch an operation mode, and apply the switched operation mode to the apparatus.

The examination object held by the examination object rack includes an examination object ID indicating attribute information (a reception number, a patient name, a requested analysis item, and the like) regarding the examination object, and the examination object rack includes a rack ID indicating rack identification information such as a rack number. Here, the rack ID means an identifier for uniquely identifying an individual rack, and examples of a representative identifier include a bar code and RFID. In addition, the rack is also provided with a hole for rack identification so that the rack can be uniquely determined from information regarding the presence and absence of a hole. The presence and absence of a hole can be identified by a transmissive or reflective sensor or the like, and this hole also corresponds to an identifier. For example, the apparatus performs conversion into a binarized number or a decimal number by using a combination of two values of the presence and absence of a hole, and thus it is possible to recognize the converted number as rack identification information such as a rack number.

The examination object rack disposed in the examination object rack insertion unit 1 is transported by the transport line 3. When the examination object rack is moved to the transport line 3, an examination object ID and an examination object rack ID are read by the ID reading unit 2 and are transmitted to the overall management computer 9. The overall management computer 9 determines in which analysis module the requested analysis item is executed, on the basis of the attribute information.

Next, the analysis modules 5, 6, and 7 will be described with reference to FIG. 14. FIG. 14 is a perspective view illustrating the entire configuration of the analysis modules. A biochemical automatic analyzer will be described as an example.

In the reaction disk 101, a plurality of reaction containers 102 each having a mixture of an examination object (sample), such as blood or urine, and a reagent are arranged on the circumference. A plurality of reagent bottles 110 can be mounted on the circumference in the reagent disk 109. A transport line 117 is installed in the vicinity of the reaction disk 101, and the transport line moves an examination object rack 116 on which examination object containers 115, such as a test tube, which accommodate a sample are loaded. Reagent dispensing mechanisms 107 and 108 that are rotatable and movable in a vertical direction are installed between the reaction disk 101 and the reagent disk 109, and include a reagent probe 107a. A syringe for reagent 118 is connected to the reagent probe 107a. A sample dispensing mechanism 111 which is rotatable and movable in a vertical direction is installed between the reaction disk 101 and the transport line 117, and includes a sample probe 111a. A sample syringe 119 is connected to the sample probe 111a. The sample probe 111a moves while drawing circular arcs centering on the rotation axis and performs the suction and discharging of an examination object from the examination object container 115 to the reaction container 102.

A cleaning mechanism 103, a light source, a spectrophotometer 104, stirring mechanisms 105 and 106, the reagent disk 109, and the transport line 117 are disposed in the vicinity of the reaction disk 101, and a cleaning pump 120 is connected to the cleaning mechanism 103. Cleaning tanks 113, 130, 131, 132, and 133 are disposed on the operation range of the reagent dispensing mechanisms 107 and 108, the sample dispensing mechanism 111, and the stirring mechanisms 105 and 106. The examination object container 115 including an examination object is loaded on the examination object rack 116 and is carried by the transport line 117.

In addition, each mechanism is connected to a controller 121, and the controller 121 controls each mechanism.

A mixed liquid of an examination object and a reagent within the reaction container 102 is irradiated with light emitted from the light source. The emitted light is received by the spectrophotometer 104, and the controller 121 calculates the concentration of a predetermined component contained in the examination object from the amount of light (the amount of transmitted light or scattered light of the mixed liquid). Meanwhile, a reagent varies depending on an analysis item. In this manner, biochemical automatic analysis is performed.

FIG. 2 illustrates a screen for setting an examination object rack ID.

Examination object type setting 201 is an area in which the range of a rack ID for examination object measurement is set with respect to five types such as a blood serum and urine. In this example, the range can be set for each type in a rack for a general examination object and a rack for an urgent examination object. Rack IDs having numbers in the 50000s are used in the rack for a general examination object, and rack IDs having numbers in the 40000s are used in the rack for an urgent examination object. Among these ranges, the range of a rack ID to be used is set for each type of examination object.

An automatic reexamination mode ON rack 202 is an area in which an automatic reexamination-validated rack ID is defined, and an automatic reexamination mode OFF rack 203 is an area in which an automatic reexamination-invalidated rack ID is defined. A maximum of four racks can be set for each of the racks 202 and 203. An operator performs setting so that the rack IDs do not overlap each other. A rack ID which is set by the operator's pressing-down of a registration button 204 is stored in a storage unit of the overall management computer 9. Meanwhile, it is possible to stop the setting of rack by pressing down a cancellation button 205, and the operator can move out of the screen.

In this manner, the automatic reexamination-validated rack ID and the automatic reexamination-invalidated rack ID are stored in the apparatus, and the examination object rack having a set rack ID serves as an operation mode switching rack. Accordingly, the operator can set any examination object rack as an operation mode switching rack.

Meanwhile, the automatic reexamination means that the apparatus automatically detects that a measurement result for a predetermined measurement item has a value falling outside a reference value, and analyzes the measurement item again.

FIG. 3 illustrates an example of the installation of an examination object rack installed in the rack insertion unit 1.

In this example, it is possible to install an examination object container for a maximum of five examination objects per examination object rack. In the rack insertion unit 1, racks having an examination object installed therein are installed in order in which the racks are desired to be measured. This is an example in a case where a plurality of examination object racks 302 to be measured in an automatic reexamination mode and an examination object rack 304 not desired to be measured in the automatic reexamination mode are provided.

In general, in a case where operation is performed in the automatic reexamination mode, racks are installed in the examination object rack insertion unit 1 in order of an automatic reexamination mode ON rack 301, the plurality of examination object racks 302 to be measured in the automatic reexamination mode, an automatic reexamination mode OFF rack 303, the examination object rack 304 not desired to be measured in the automatic reexamination, and an automatic reexamination mode ON rack 305.

At this time, more preferably, when a mark for distinction from an examination object rack (302, 304) for measurement is attached to the automatic reexamination mode ON racks 301 and 303 and the automatic reexamination mode OFF rack 302, it is easy to confirm the racks for the automatic reexamination mode before the insertion of the racks into the apparatus, and it is possible to prevent an erroneous operation.

When measurement is started from an operation screen of the operation unit 10 after the racks are installed in the insertion unit, the state of the apparatus transitions from a standby state to a measurement state. The racks installed in the rack insertion unit 1 are transported by the transport line 3 in order of the racks 301, 302, 303, 304, and 305, and are read by the ID reading unit 2 so that rack IDs and examination object IDs of examination objects installed in the racks are recognized. Meanwhile, when an initial state is set to be automatic reexamination validation in advance in a standby state, the automatic reexamination mode ON rack 301 is not necessary.

The rack 301 is read by the ID reading unit 2, and thus the apparatus recognizes that racks to be subsequently carried thereinto are racks in which an automatic reexamination mode is valid, and applies an automatic reexamination validation mode. After a while, the rack 303 is read by the ID reading unit 2, and thus the apparatus recognizes that racks to be subsequently carried thereinto are racks in which an automatic reexamination mode is invalid, and applies an automatic reexamination invalidation mode. In addition, after a while, the rack 305 is read by the ID reading unit 2, and thus the apparatus recognizes that racks to be subsequently carried thereinto are racks in which an automatic reexamination mode is valid, and applies an automatic reexamination validation mode as described above. In this manner, it is possible to apply an automatic reexamination invalidation mode to only the rack 304.

FIG. 4 is a diagram illustrating a flow of rack ID identification processing of an automatic reexamination switching rack.

In step 401, the ID reading unit 2 reads a rack ID which is transported. In step 402, the control unit determines the type of rack from the read rack ID and rack ID information which is set in the rack setting screen of FIG. 2.

When the rack ID indicates an automatic reexamination mode ON rack, the control unit sets an automatic reexamination mode to be in an on-state in step 403. Thereafter, in step 405, the rack is transported to the rack recovery unit.

When the rack ID indicates an automatic reexamination mode OFF rack, the control unit sets the automatic reexamination mode to be in an off-state in step 404. Thereafter, in step 405, the rack is transported to the rack recovery unit.

In step 402, when the rack ID indicates a rack for a general examination object or a rack for an urgent examination object, processing of a first measurement rack of FIG. 5 is executed.

Meanwhile, the rack does not have an examination object container, which is a measurement object, mounted thereon, and thus is transported to the rack recovery unit without stopping by in any of the analysis modules 5, 6, and 7.

FIG. 5 is a diagram illustrating a flow of rack processing during first measurement.

In step 502, the control unit confirms the automatic reexamination mode determined in FIG. 4 in units of examination object racks recognized.

In a case where the automatic reexamination mode is turned on, the control unit causes the storage unit to store a fact that rack automatic reexamination of a measurement rack is valid in rack measurement management information for managing the measurement rack, in step 511. In this example, the storage may be performed in units of racks, or automatic reexamination information may be stored on the basis of examination object measurement information managed in units of examination objects installed in the rack.

In a case where the automatic reexamination mode is turned off, the control unit causes the storage unit to store a fact that the rack automatic reexamination of the rack is invalid, in step 512.

In step 503, it is determined whether or not there is a measurement request item with respect to all examination objects installed in the examination object racks.

In a case where there is a request item with respect to the examination object racks, a rack transport schedule for determining to which analysis module and in what order the examination object racks are to be transported on the basis of the request item is created, in step 504. In step 505, the examination object racks are transported to necessary analysis modules in order on the basis of the rack transport schedule. Examination objects of the examination object racks transported to the respective analysis modules are measured for necessary request items in the analysis modules.

After the transport of the examination objects to all of the analysis modules required for measurement is terminated, the control unit confirms automatic reexamination information of the examination object racks in step 506. In a case where the automatic reexamination is turned on, the control unit transports the rack to the rack standby unit through the transport line and causes the rack to standby in the rack standby unit until a first measurement result is output, in step 507.

In a case where the automatic reexamination information is turned off, the control unit transports the rack to the rack recovery unit without causing the rack to standby in the rack recovery unit, in step 508. The rack transported to the rack recovery unit can be taken out from the apparatus by an operator.

FIG. 6 is a diagram illustrating a flow of rack processing during reexamination measurement.

When a measurement result corresponding to one examination object is output, a reexamination request is created on the basis of the measurement result in step 602.

In a case where rack automatic reexamination of the examination object is turned off in step 603, the rack has been already recovered, and thus the processing is terminated (step 604).

In a case where the rack automatic reexamination is turned on, the control unit determines in step 605 whether all measurement results have been output (or whether measurement has been terminated) for the examination object mounted on the rack.

In a case where all measurement results have not been output for the examination object of the rack, the rack continues standing by in the rack standby unit in step 605.

In a case where all measurement results have been output for the examination object of the rack, the control unit determines in step 607 whether or not there is a reexamination request for all examination objects of the rack. Here, the control unit confirms whether or not measurement results of respective items fall within a reference value, and determines that there is a reexamination request in a case where it is determined that even one item falls outside the reference value.

In a case where there is no reexamination request, the rack is transported from the rack standby unit to the rack recovery unit in step 610. In a case where there is a reexamination request, a rack transport schedule for determining to which analysis module and in what order the examination object racks are to be transported on the basis of the reexamination request item is created, in step 608.

In step 609, the examination object racks are transported to necessary analysis modules in order on the basis of the rack transport schedule. The examination objects of the examination object racks transported to the respective analysis modules are measured for necessary request items in the analysis modules.

FIG. 7 is a diagram illustrating an automatic reexamination state display screen which is displayed on the display unit.

Reference numeral 701 denotes automatic reexamination mode display, and the control unit outputs the state of automatic reexamination to an area which is displayed at all times like the state of the apparatus and a clock display.

The automatic reexamination mode display is set to be automatic reexamination ON display when an automatic reexamination ON rack is recognized, and is set to be automatic reexamination OFF display when an automatic reexamination OFF rack is recognized. Thereby, an operator can previously confirm an automatic reexamination mode of an examination object rack to be inserted next. Since this display is switched for every detection of an operation mode switching rack in a measurement state, it is possible to confirm the present automatic reexamination mode in real time. Meanwhile, in a configuration in which automatic reexamination ON or OFF can be set in a standby state as initial setting, the initial setting may be displayed as the state of automatic reexamination, regardless of whether or not the operation mode switching rack has been recognized.

Reference numeral 702 indicates the state of validation or invalidation of automatic reexamination for each examination object mounted on a rack during measurement. The validation and invalidation states are displayed on the basis of rack automatic reexamination information. An examination object ID or a rack ID and the validation or invalidation of automatic reexamination are displayed in association with each other, and thus it is possible to confirm whether or not an examination object can be taken out immediately after the examination object or the rack is transported to the analysis module. That is, when the invalidation of automatic reexamination is displayed, the operator can recognize that the corresponding examination object or rack can be immediately taken out.

As described so far, the operation mode switching rack can switch between a mode in which the examination object rack stands by in the examination object rack standby unit until a measurement result in the analysis module is output in a case where the automatic reexamination is valid and a mode in which the examination object rack is recovered to the examination object rack recovery unit without standing by in the examination object rack standby unit in a case where the automatic reexamination is invalid.

As described above, the first embodiment has been described. The examination object rack is defined as an operation switching rack, and it is possible to notify the apparatus of an operation switching timing by the operation switching rack by using an ID reading unit of the related art. Accordingly, it is possible to perform switching between the validation and invalidation of an automatic reexamination mode in a measurement state without transitioning from the measurement state to a standby state as in the related art. In addition, in the apparatus having a configuration in which a rack ID is set for each type of examination object, it is not necessary to perform range setting for a rack ID by multiplying the types of examination objects and the validation or invalidation of automatic reexamination together, which does not result in the operator's erroneous arrangement of the examination objects which is caused by the complication of range setting of a rack ID. In addition, operation is dynamically switched by the operation switching rack, but the present operation mode is displayed on the display unit. Thus, the operator can operate an operation mode with respect to a desired examination object rack without fail.

Example 2

A second embodiment will be described. An operation mode in this embodiment is a data abnormal value check. Here, the data abnormal value check refers to a check regarding whether or not a measurement result is an abnormal value during the output of the measurement result in an analysis module.

For example, the data abnormal value check is not performed on an examination object, such as a dialysis patient examination object, which has a data abnormal value at all times, and thus it is possible to prevent wasteful automatic reexamination measurement and to shorten the time and prevent a wasteful use of the examination object. For this reason, it may be more useful in a case where a data abnormality check is not performed depending on a rack. An embodiment in such a case will be described.

FIGS. 8 to 10 relate to an embodiment in which an operation mode switching rack is used for switching between the execution and non-execution of a data abnormal value check.

FIG. 8 illustrates main portions of a screen for setting a rack ID of a switching rack of a data abnormal value check. The setting of the automatic reexamination mode in FIG. 2 being replaced with that in FIG. 8 is displayed as a rack setting screen.

A data abnormal value check ON rack 801 is an area in which a data abnormal value check-validated rack ID is defined, and a data abnormal value check OFF rack 802 is an area in which an automatic reexamination-invalidated rack ID is defined. A maximum of four racks can be set for each of the racks 801 and 802. An operator performs setting so that the rack IDs do not overlap each other. A rack ID which is set by the operator's pressing-down of a registration button 204 is stored in a storage unit of an overall management computer 9.

In a case where a measurement result is the execution of a data abnormal value check, racks of examination objects desired to be measured in a case of the execution of the data abnormal value check are inserted side by side into the apparatus in order behind the data abnormal value check ON rack.

In a case where a measurement result is the non-execution of a data abnormal value check, racks of examination objects to be measured in a case of the non-execution of the data abnormal value check are inserted side by side into the apparatus in order behind the data abnormal value check OFF rack.

FIG. 9 is a diagram illustrating a flow of rack ID identification processing of a switching rack of a data abnormal value check.

In step 811, an ID reading unit 2 reads a rack ID which is transported. In step 812, a control unit determines the type of rack from the read rack ID and rack ID information which is set in the rack setting screen of FIG. 8.

When the rack ID indicates a data abnormal value check ON rack, the control unit sets an abnormal value check mode to be in an on-state in step 813. Thereafter, in step 815, the rack is transported to a rack recovery unit.

When the rack ID indicates a data abnormal value check OFF rack, the control unit sets the abnormal value check mode to be in an off-state in step 814. Thereafter, in step 815, the rack is transported to the rack recovery unit.

Meanwhile, the rack does not have an examination object container, which is a measurement object, mounted thereon, and thus is transported to the rack recovery unit without stopping by in any of analysis modules 5, 6, and 7.

When the rack ID is a rack for a general examination object or a rack for an urgent examination object in step 812, the control unit determines the data abnormal value check mode in units of recognized examination object racks in step 816.

In a case where the data abnormal value check mode is turned on, the control unit causes the storage unit to store a fact that a rack abnormal value check of a measurement rack is valid in rack measurement management information for managing the measurement rack, in step 817. In this example, the storage may be performed in units of racks, or the validation or invalidation of an abnormal value check may be stored on the basis of examination object measurement information managed in units of examination objects installed in the rack.

In a case where the data abnormal value check mode is turned off, the control unit causes the storage unit to store a fact that the rack abnormal value check is invalid, in step 818.

FIG. 10 is a diagram illustrating a flow of data abnormal value check processing during the output of a measurement result.

When a measurement result for one item of an examination object of a rack is output (step 851), it is determined in step 852 whether or not a rack abnormal value check is valid or invalid.

When the rack abnormal value check is invalid, the control unit does not perform the data abnormal value check. That is, even when a measurement result for a predetermined item has a value falling outside a reference value, the measurement result is output without displaying an alarm indicating the abnormality of data.

When the rack abnormal value check is valid, the control unit performs the data abnormal value check in step 853. In a case where the output measurement result is abnormality (falling outside the reference value) in the data abnormal value check, a data alarm indicating data abnormality is added to the measurement result. In step 854, the measurement result is registered, and a reexamination request is registered when an automatic reexamination mode is valid. This is because the reexamination request is registered on the basis of the data alarm indicating data abnormality in a case where the automatic reexamination mode is valid.

Meanwhile, when the rack abnormal value check is invalid, a data alarm indicating data abnormality is not added, and thus a reexamination request is not registered. This is because the reexamination request is registered on the basis of the data alarm.

When the reexamination request is registered for one or more items among the examination objects of the examination object racks after measurement for all of the examination object racks is completed, automatic reexamination measurement is performed. Any reexamination request is not registered, automatic reexamination is not performed, and the racks are recovered.

As described so far, the operation mode switching rack can switch between a mode in which a data alarm is added to a measurement result in an analysis module in a case where a data abnormal value check is valid and the measurement result is abnormal and a mode in which a data alarm is not added to the measurement result in the analysis module in a case where the data abnormality check is invalid and the measurement result is abnormal.

As described above, the second embodiment has been described. The examination object rack is defined as an operation switching rack, and it is possible to notify the apparatus of an operation switching timing by the operation switching rack by using an ID reading unit of the related art. Accordingly, it is possible to perform switching between the validation and invalidation of a data abnormal value check in a measurement state. Thereby, the data abnormal value check is invalidated even when an automatic reexamination mode is a valid operation mode, it is possible to prevent wasteful automatic reinspection and to shorten the time and prevent a wasteful use of the examination object with respect to an examination object, such as a dialysis patient examination object, which has a data abnormal value at all times.

The same effects as those in the first embodiment are obtained in terms of preventing automatic reexamination. However, in a case of the second embodiment, a data alarm is not added, and thus it is possible to prevent an operator from performing reexamination and the like due to erroneous manual reinsertion into the apparatus in response to an alarm.

Meanwhile, since a description is repeated, and thus the description will be omitted. However, also in this embodiment, it is also preferable to apply the display of validation or invalidation of the present data abnormal value check in real time and the display of association between an examination object ID or a rack ID and the validation or invalidation of a data abnormal value check, as in FIG. 7.

Example 3

A third embodiment will be described. An operation mode in this embodiment is a mode in which an apparatus performs inquiry about a measurement request item together with a high order host. For example, in a case where an examination object desired to be measured in accordance with a request item, defined in advance within an apparatus, and an examination object desired to be measured in accordance with a request item received from a high order host through a network are mixedly present, switching between the execution and non-execution of inquiry of a host request may be performed in accordance with an examination object rack. In this case, it is possible to eliminate a wasteful host inquiry or a processing time of a response received from a host with respect to the examination object to be measured in accordance with the request item defined in advance within the apparatus, and to improve a throughput of the measurement. In a case where the host does not include the corresponding examination object information with respect to a request inquiry by the apparatus, the host may not return a response to the apparatus, and the apparatus waits for measurement until the time-out of reception. Effectiveness is exhibited in such a case.

FIGS. 11 to 13 relate to an embodiment in which an operation mode switching rack is used for switching between the execution and non-execution of high order host request inquiry.

An overall management computer 9 is connected to a high order host system (hereinafter, also simply referred to as a host) through a network, and has a system configuration in which a request item is inquired from the high order host system about an examination object recognized by the apparatus, and the apparatus receives a measurement request item from the high order host system and performs measurement.

FIG. 11 illustrates main portions of a screen for setting a rack ID of a switching rack of a host request inquiry. The setting of the automatic reexamination mode in FIG. 2 being replaced with that in FIG. 11 is displayed as a rack setting screen.

A host request inquiry ON rack 901 is an area in which a host request inquiry-validated rack ID is defined, and a host request inquiry OFF rack 902 is an area in which a host request inquiry-invalidated rack ID is defined. A maximum of four racks can be set for each of the racks 901 and 902. An operator performs setting so that the rack IDs do not overlap each other. A rack ID which is set by the operator's pressing-down of a registration button 204 is stored in a storage unit of the overall management computer 9.

In a case of examination objects desired to be measured in accordance with a request item designated by a host, racks of the examination objects desired to be measured in accordance with the request item designated by the host are inserted side by side into the apparatus in order behind a host inquiry ON rack.

In a case of examination objects desired to be measured in accordance with a request item registered within the apparatus rather than a request received from the host, racks of the examination objects desired to be measured in accordance with the request item registered within the apparatus are inserted side by side into the apparatus in order behind a host inquiry OFF rack.

FIG. 12 is a diagram illustrating a flow of rack ID identification processing of a switching rack of a host request inquiry.

In step 911, an ID reading unit 2 reads a rack ID which is transported. In step 912, a control unit determines the type of rack from the read rack ID and rack ID information which is set in the rack setting screen of FIG. 11.

When the rack ID indicates a host request inquiry ON rack, the control unit sets a host inquiry mode to be in an on-state in step 913. Thereafter, in step 915, the rack is transported to a rack recovery unit.

When the rack ID indicates a host request inquiry OFF rack, the control unit sets the host inquiry mode to be in an off-state in step 914. Thereafter, in step 915, the rack is transported to the rack recovery unit.

Meanwhile, the rack does not have an examination object container, which is a measurement object, mounted thereon, and thus is transported to the rack recovery unit without stopping by in any of analysis modules 5, 6, and 7.

When the rack ID is a rack for a general examination object or a rack for an urgent examination object in step 912, the control unit determines the host inquiry mode in units of recognized examination object racks in step 916.

In a case where the host inquiry mode is turned on, the control unit stores a fact that a host inquiry of a measurement rack is valid (executed) in rack measurement management information for managing the measurement rack, in step 917. In this example, the storage may be performed in units of racks, or the validation or invalidation of a host inquiry may be stored on the basis of examination object measurement information managed in units of examination objects installed in the rack.

In a case where the host inquiry mode is turned off, the storage unit stores a fact that the host inquiry is invalid, in step 918.

FIG. 13 is a diagram illustrating a flow of host request inquiry processing in units of racks.

In a case where an inserted rack is a general rack or an urgent rack (step 951), a process of applying a request item to the number of examination objects mounted on the rack is performed (step 952).

In a case where host inquiry information of the rack is invalid in step 953, a measurement request item is not inquired from a host. That is, measurement is executed in accordance with a request item registered within the apparatus.

In a case where the rack host inquiry of the rack is valid, a request for the examination objects is inquired from the host in step 954, and the request item received from the host is applied in step 955, thereby performing measurement in accordance with the request item.

Request information registered in advance through the screen or the like of the apparatus is applied to the examination objects in step 956. At this time, in a case where the request item from the host is applied in step 954, both the pieces of request information are applied. A flow thereof is performed on all of the examination objects mounted on the rack (step 958). Thereafter, a rack transport schedule is created on the basis of the applied request information, and is transported to a target analysis module.

In addition, also in a reexamination creating process (step 602) after a first measurement result is output, a reexamination request is created through the request item application process of FIG. 13. For example, when there is a measurement request item added in response to a request inquiry from the host, a reexamination request is created on the basis of the added measurement request item also in the reexamination request.

As described so far, the high order host system connected to the apparatus through a network is further included, the automatic analyzer inquires a measurement request item corresponding to an examination object container from the high order host system, and the corresponding measurement request item is received from the high order host system, whereby the measurement request item is measured in the analysis module. An operation mode is a mode regarding whether or not the measurement request item is inquired from the high order host system, and an operation mode switching rack is a rack that switches between the execution and non-execution of inquiry of the measurement request item from the high order host system.

In addition, the operation mode switching rack can switch between a mode in which the inquiry from the high order host system is performed and a mode in which a measurement request item registered in the automatic analyzer is measured by the analysis module without performing inquiry from the high order host system.

As described above, the third embodiment has been described. The examination object rack is defined as an operation switching rack, and it is possible to notify the apparatus of an operation switching timing by the operation switching rack by using an ID reading unit of the related art. Accordingly, it is possible to perform switching between the validation and invalidation of a request inquiry of a measurement item from the host in a measurement state. Thereby, in a case where a request item defined in advance within the apparatus and an examination object desired to be measured in accordance with a request item received from a high order host through a network are mixedly present, it is possible to perform operation by switching between the execution and non-execution of inquiry of a host request in accordance with an examination object rack and to give a request for a measurement item corresponding to conditions in a measurement state.

As described above, the first to third embodiments have been described. As described in the embodiments, the invention includes a detection unit that detects an operation mode switching rack inserted into an insertion unit, and a control unit that switches an operation mode stored in a storage unit on the basis of the detection of the operation mode switching rack by the detection unit. The control unit applies the switched operation mode to an examination object rack transported from the insertion unit to a transport line after the operation mode switching rack.

In the embodiments, an ID reading unit has been described as an example of the detection unit. However, the detection unit is not limited to the ID reading unit as long as the apparatus can recognize the operation mode switching rack. For example, the shape or color of an operation mode switching rack is made different from that of a normal examination object rack, and a shape or color sensor that detects the operation mode switching rack can also be used. In a case of a shape sensor, for example, the height of the operation mode switching rack is made larger or smaller than the height of the normal examination object rack, and it is possible to cause the apparatus to recognize the operation mode switching rack in accordance with the height. An example of the sensor is a height sensor including a plurality of light sources and a light receiving unit in a vertical direction. A distinction between the turn-on and turn-off of the operation mode switching rack can be made in accordance with two-stage heights. In addition, in a case of a color sensor, the color of the operation mode switching rack is made different from the color of the normal examination object rack, and it is possible to cause the apparatus to recognize the operation mode switching rack in accordance with the color. A distinction between the turn-on and turn-off of the operation mode switching rack can be made in accordance with two colors. In a case where such a shape or color sensor is used, it is possible to perform the same control as that of the ID reading unit as long as an area for setting height or color in a rack setting screen is provided.

In addition, the detection unit reads an operation mode switching ID attached to a container mounted on an examination object rack instead of a rack ID attached to the rack, and thus the control unit may switch an operation mode stored in the storage unit. The operation mode switching ID is an identifier such as a barcode having unique numerals for switching an operation mode stored therein or RFID. In this case, the operation mode switching rack is an examination object rack on which a container having an operation mode switching ID attached thereto is mounted, and the detection unit detecting the operation mode switching rack can be considered to be a detection unit that detects the operation mode switching ID. That is, in this specification, a case where the operation mode switching rack is detected also includes a case where the ID of the container mounted on the rack is detected, in addition to a case where an actual rack is detected.

However, it is useful in that the switching of an operation mode can be performed using a simple method without newly providing the shape or color sensor by using a rack ID.

In addition, in the embodiments, a description has been given on the assumption that the operation mode switching rack is an operation mode-validated or invalided rack. However, the invention is not limited to a choice between validation and invalidation. For example, in a case of reexamination, the operation mode switching rack may be a rack that switches between a mode in which the reexamination is performed in the same analysis module as the first analysis module and a mode in which reexamination is performed in a different analysis module.

In addition, it is preferable that the control unit switches the display of an operation mode displayed on a display unit on the basis of the detection of the operation mode switching rack by the detection unit. This is because the operator can perform operation while confirming the present operation mode.

In addition, it is preferable that the control unit causes the storage unit to store the switched operation mode for each examination object rack or each examination object container mounted on the examination object rack with respect to the examination object rack transported after the operation mode switching rack. Thereby, it is possible to display an operation mode applied for each examination object rack or each examination object container.

In addition, a description has been given of three types of operation modes of an automatic reexamination mode, a mode in which it is checked whether or not a measurement result has an abnormal value, and a mode regarding whether or not a measurement request item is inquired from a high order host system in a case where the high order host system is present, but is not limited thereto. Various applications can be made.

In addition, in the embodiments, a description has been given of an example in which a distinction between a rack for a general examination object and a rack for an urgent examination object is made for the operation mode switching rack. However, two types of an operation mode switching rack for the rack for a general examination object and an operation mode switching rack for the rack for an urgent examination object may be used.

In addition, in the embodiments, an ON rack and an OFF rack have been described. However, a switching rack that reverses a mode from ON to OFF and from OFF to ON may be registered in the apparatus.

In addition, in the embodiments, the automatic analyzer including the plurality of analysis modules has been described as an example. However, the invention can also be applied to an automatic analyzer including a single analysis module.

In addition, a description has been given of an example in which the analysis module is a biochemical automatic analyzer. However, the invention can also be applied in a case where the analysis module is an immunity automatic analyzer or a coagulation automatic analyzer.

In addition, a description has been given of an example of a rack on which a plurality of examination object containers can be mounted. However, the invention can also be applied to a rack on which one examination object container is mounted.

In addition, the invention described in claims is not limited to the embodiments, and includes various embodiments without departing from the scope of the invention.

REFERENCE SIGNS LIST

1: EXAMINATION OBJECT RACK INSERTION UNIT (RACK INSERTION UNIT)
2: ID READING UNIT (DETECTION UNIT)
3: TRANSPORT LINE
4: EXAMINATION OBJECT RACK STANDBY UNIT (RACK STANDBY UNIT)
5, 6, 7: ANALYSIS MODULE
8: EXAMINATION OBJECT RACK RECOVERY UNIT (RACK RECOVERY UNIT)
9: OVERALL MANAGEMENT COMPUTER
10: OPERATION UNIT
11: DISPLAY UNIT

The invention claimed is:

1. An analysis method of an automatic analyzer, the automatic analyzer including an insertion unit into which a rack is inserted, a transport line that transports the rack, a detection unit that detects a rack identifier from the rack or an attribute from a sample container which accommodates therein a sample as an object to be examined and which is mounted on the rack, an analysis module that includes a light source and a spectrometer which measures a measurement value to analyze a sample, a rack standby unit in which the rack stands by, and a rack recovery unit that recovers the rack, wherein a rack stands by in the rack standby unit until a measurement result in the analysis module is output and is then transported to the rack recovery unit, the analysis method comprising:

a step of transporting the rack from the rack insertion unit to the transport line, making the transported rack stand by in the rack standby unit until the measurement result in the analysis module is output, and then transporting the rack to the rack recovery unit according to a first mode of automatic reexamination;

a step of detecting an identifier from the rack or an attribute from the sample container accommodating the sample and mounted on the rack;

a step of determining that a predetermined rack of interest is transported from the rack insertion unit to the transport line, and in response to determining that the predetermined rack of interest is transported from the rack insertion unit to the transport line, change the first mode to a second mode of invalidating the automatic reexamination;

a step of transporting a subsequent rack transported subsequent to the predetermined rack of interest to the analysis module for examination;

a step of determining the examination mode is the second mode; and a step of transporting the subsequent rack from the analysis module to the rack recovery unit without standing by in the rack standby unit according to the second mode.

2. The analysis method according to claim 1, wherein the detection unit is an identification (ID) reading unit that reads a rack ID attached to a rack or a sample ID attached to a sample container, to thereby detect the rack or the sample container.

3. The analysis method according to claim 1, wherein the detection unit is a shape or color sensor that detects a rack from a shape or color thereof.

4. The analysis method according to claim 1, wherein a rack mounts thereon one sample container or a plurality of sample containers.

5. The analysis method according to claim 1, wherein a sample is categorized into an urgent sample and a general sample, and wherein the analysis method further comprises;

when the detection unit detects an identifier from the rack of interest or an attribute from the sample container of interest:

a step of, when a rack for an urgent sample transported subsequent to the rack of interest is transported from the rack insertion unit to the transport line, transporting the rack for the urgent sample without standing by in the rack standby unit; and a step of, when a rack for a general sample transported subsequent to the rack of interest is transported from the rack insertion unit to the transport line, making the rack for the general sample stand by in the rack standby unit until a measurement result in the analysis module is output.

6. The analysis method according to claim 1, wherein a sample is categorized into an urgent sample and a general sample, and wherein the analysis method further comprises: when the detection unit detects an identifier from the rack of interest or an attribute from the sample container of interest:

a step of, when a rack for a general sample transported subsequent to the rack of interest is transported from the rack insertion unit to the transport line, transporting the rack for the general sample to the rack recovery unit without standing by in the rack standby unit; and a step of, when a rack for an urgent sample transported subsequent to the rack of interest is transported from the rack insertion unit to the transport line, making the rack for the urgent sample stand by in the rack standby unit until a measurement result in the analysis module is output.

7. An analysis method of an automatic analyzer, the automatic analyzer including a rack insertion unit into which a rack is inserted, a transport line that transports the rack, a detection unit that detects a rack identifier from the rack or an attribute from a sample container which accommodates therein a sample as an object to be examined and which is mounted on the rack, an analysis module that includes a light source and a spectrometer which measures a measurement value to analyze the sample, a rack standby unit in which the rack stands by, a rack recovery unit that recovers the rack, wherein the rack is transported from the rack insertion unit to the transport line, and after a measurement result in the analysis module is output, the rack is then transported to the rack recovery unit without standing by in the rack standby unit, the analysis method comprising:

a step of transporting the rack from the rack insertion unit to the transport line, and, after the measurement result in the analysis module is output, transporting the rack to the rack recovery unit without standing by in the rack standby unit according to a second mode;

a step of detecting an identifier from the rack or an attribute from the sample container accommodating the sample and mounted on the rack;

a step of determining that a predetermined rack of interest is transported from the rack insertion unit to the transport line, and in response to determining that the predetermined rack of interest is transported from the rack insertion unit to the transport line, change the second mode to a first mode;

a step of transporting a subsequent rack transported subsequent to the predetermined rack of interest to the analysis module for examination;

a step of determining the examination mode is the first mode; and a step of transporting the subsequent rack from the analysis module to the rack standby unit and making the subsequent rack stand by in the rack standby unit until the measurement result in the analysis module is output, and then transporting the subsequent rack to the rack recovery unit according to the first mode.

8. The analysis method according to claim 2, wherein the detection unit is an identification (ID) reading unit that reads a rack ID attached to a rack or a sample ID attached to a sample container, to thereby detect the rack or the sample container.

9. The analysis method according to claim 2, wherein the detection unit is a shape or color sensor that detects a rack from a shape or color thereof.

10. The analysis method according to claim 2, wherein a rack mounts thereon one sample container or a plurality of sample containers.

11. The analysis method according to claim 2, wherein a sample is categorized into an urgent sample and a general sample, and wherein the analysis method further comprises:

when the detection unit detects an identifier from the rack of interest or an attribute from the sample container of interest:

a step of, when a rack for an urgent sample transported subsequent to the rack of interest is transported from the rack insertion unit to the transport line, transporting the rack for the urgent sample without standing by in the rack standby unit; and a step of, when a rack for a general sample transported subsequent to the rack of interest is transported from the rack insertion unit to the transport line, making the rack for the general sample stand by in the rack standby unit until a measurement result in the analysis module is output.

12. The analysis method according to claim 2, wherein a sample is categorized into an urgent sample and a general sample, and wherein the analysis method further comprises, when the detection unit detects an identifier from the rack of interest or an attribute from the sample container of interest:

a step of, when a rack for a general sample transported subsequent to the rack of interest is transported from the rack insertion unit to the transport line, transporting the rack for the general sample to the rack recovery unit without standing by in the rack standby unit; and a step of, when a rack for an urgent sample transported subsequent to the rack of interest is transported from the rack insertion unit to the transport line, making the rack for the urgent sample stand by in the rack standby unit until a measurement result in the analysis module is output.

* * * * *